(12) United States Patent
Malec

(10) Patent No.: US 8,455,396 B2
(45) Date of Patent: Jun. 4, 2013

(54) ALKALI METAL GLYPHOSATE COMPOSITIONS

(75) Inventor: Andrew Malec, Chicago, IL (US)

(73) Assignee: Stepan Company, Northfield, IL (US)

( * ) Notice: Subject to any disclaimer, the term of this patent is extended or adjusted under 35 U.S.C. 154(b) by 56 days.

(21) Appl. No.: 13/179,775

(22) Filed: Jul. 11, 2011

(65) Prior Publication Data

US 2013/0017953 A1    Jan. 17, 2013

(51) Int. Cl.
- *A01N 57/18* (2006.01)
- *A61K 31/13* (2006.01)

(52) U.S. Cl.
USPC .................. 504/206; 514/663; 514/975

(58) Field of Classification Search
None
See application file for complete search history.

(56) References Cited

U.S. PATENT DOCUMENTS

| | | |
|---|---|---|
| 5,226,943 A | 7/1993 | Hulshof |
| 5,616,811 A | 4/1997 | Vipond et al. |
| 5,668,085 A | 9/1997 | Forbes et al. |
| 5,710,103 A | 1/1998 | Magin et al. |
| 5,750,468 A | 5/1998 | Wright et al. |
| 5,948,421 A | 9/1999 | Okano et al. |
| 5,998,332 A | 12/1999 | Sato et al. |
| 6,008,158 A | 12/1999 | Hasebe et al. |
| 6,277,788 B1 | 8/2001 | Wright |
| 6,455,473 B2 | 9/2002 | Wright |
| RE37,866 E | 10/2002 | Wright et al. |
| 6,475,953 B1 | 11/2002 | Ward et al. |
| 6,706,666 B2 | 3/2004 | Hasebe et al. |
| 6,767,863 B2 | 7/2004 | Holger |
| 6,881,707 B2 | 4/2005 | Howat et al. |
| 6,887,830 B2 | 5/2005 | Stridde et al. |
| 6,992,046 B2 | 1/2006 | Bramati et al. |
| 7,049,270 B2 | 5/2006 | Lennon et al. |
| 7,135,437 B2 | 11/2006 | Pallas et al. |
| 7,223,718 B2 | 5/2007 | Smiley |
| 7,316,990 B2 | 1/2008 | Tank |
| 2002/0160917 A1 | 10/2002 | Ottaway et al. |
| 2003/0032558 A1 | 2/2003 | Stridde et al. |
| 2003/0096708 A1* | 5/2003 | Agbaje et al. .......... 504/365 |
| 2003/0104943 A1 | 6/2003 | Lennon et al. |
| 2005/0170965 A1 | 8/2005 | Bramati et al. |
| 2006/0240985 A1 | 10/2006 | Moreno |
| 2009/0018018 A1 | 1/2009 | Gioia et al. |
| 2009/0215626 A1 | 8/2009 | Elsik et al. |
| 2009/0318294 A1* | 12/2009 | Malec et al. .......... 504/206 |
| 2010/0016163 A1 | 1/2010 | Keiper et al. |
| 2010/0113274 A1 | 5/2010 | Hemminghaus et al. |
| 2010/0160162 A1 | 6/2010 | Becher et al. |
| 2010/0273654 A1 | 10/2010 | Li et al. |
| 2010/0311591 A1 | 12/2010 | Yeritsyan |
| 2010/0331182 A1 | 12/2010 | Zhang et al. |
| 2011/0009269 A1 | 1/2011 | Gioia et al. |
| 2011/0105328 A1 | 5/2011 | Chavant et al. |
| 2012/0065068 A1 | 3/2012 | Downer et al. |

FOREIGN PATENT DOCUMENTS

WO    WO 2007054540    *   5/2007

OTHER PUBLICATIONS

Lei, Yabin, "Applications of Ether Amine Surfactants in Agricultural Formulations: The Known and Unexplored", Journal of ASTM International vol. 2, No. 7 Jul./Aug. 2005, 1-11.

International Search Report and Written Opinion, mailed Sep. 17, 2012, for PCT/US12/45972 (applicant: Stepan Company).

* cited by examiner

*Primary Examiner* — Alton Pryor
(74) *Attorney, Agent, or Firm* — Dilworth IP LLC

(57) ABSTRACT

Aqueous alkali metal glyphosate compositions are disclosed. The compositions comprise an aqueous concentrate of an alkali metal glyphosate, a surfactant blend comprising an etheramine component, and an optional water-miscible solvent. A mixture of the surfactant blend and solvent is gel-free and monophasic. Adjusting the pH of the aqueous concentrate to be within the range of 4.0 to 4.5 surprisingly enables preparation of a highly concentrated aqueous alkali metal glyphosate composition having good elevated temperature stability and a high cloud point. For instance, a 540 g.a.e./L formulation comprising the composition exhibits good stability at 54° C. Gel-free, monophasic surfactant blends useful in the glyphosate compositions are also disclosed.

21 Claims, No Drawings

ALKALI METAL GLYPHOSATE COMPOSITIONS

FIELD OF THE INVENTION

The invention relates to alkali metal glyphosate compositions. In particular, the invention relates to high-load glyphosate compositions that have good stability at elevated temperature.

BACKGROUND OF THE INVENTION

N-Phosphonomethylglycine ("glyphosate") is a well-known, post-emergent, foliar-applied herbicide. When glyphosate formulations are applied to green leaves or stems, glyphosate moves through the plant so the entire plant dies. Glyphosate works by disrupting a plant enzyme, EPSP synthase, involved in the production of amino acids that are essential to plant growth. Because the enzyme is not present in humans or animals, glyphosate has very low toxicity to humans or animals.

Glyphosate is typically formulated and applied in the form of a water-soluble agriculturally acceptable salt, preferably as a monobasic salt. The most widely employed salt of glyphosate is the isopropylamine (IPA) salt. The salts of glyphosate are generally prepared by partial or complete neutralization of the acid with an appropriate base. Glyphosate salt formulations are provided in concentrate, dilute (ready to use) and solid (granulate) forms.

Surfactants are employed as adjuvants in glyphosate salt formulations to enhance herbicidal effectiveness. Surfactants help the formulations adhere to the surfaces of leaves and thus enhance penetration. The surfactant may be blended with the glyphosate salt in the concentrate or solid forms or may be added by the user to the diluted spray solution. A wide variety of surfactants have been taught as suitable for use, and cationic surfactants, in particular, have been widely used. See, for example, the exhaustive list of surfactant types taught in U.S. Pat. Nos. 7,049,270 and 7,135,437.

Etheramine alkoxylates are known surfactants for glyphosate salt formulations. For example, U.S. Pat. No. 5,750,468 teaches that these compositions provide a less-irritating alternative to ethoxylated tallowamines. The reference teaches that quaternized or oxidized analogs of the etheramine alkoxylates can be used instead of the etheramine alkoxylates. The '468 patent also teaches that the etheramine alkoxylates are especially well-suited for use with IPA glyphosates and limits its examples to them. U.S. Pat. No. 6,277,788 also discloses etheramine alkoxylates in glyphosates, and explains the advantages of using monoethylamine (MEA) salts instead of IPA salts for making highly concentrated aqueous glyphosate compositions. U.S. Pat. Appl. Publ. No. 2010/0160162 suggests using a blend of an etheramine alkoxylate and a traditional tallowamine surfactant to improve herbicidal selectivity and reduce the tendency of the surfactant to cause eye irritation.

Since the initial suggestion to use etheramine alkoxylates in glyphosates (in the '468 patent), they have been listed as possible surfactant components in similar compositions, usually in combination with other surfactants. For instance, etheramine ethoxylates have been taught for use in combination with diamines or polyamines (U.S. Pat. Appl. Publ. No. 2003/0096708), alkylbetaines or alkyl(amido-alkyl)betaines (U.S. Pat. Appl. Publ. No. 2004/0224846), amidoalkylamines (U.S. Pat. Appl. Publ. No. 2010/0113274), and fatty amine oxides (U.S. Pat. Appl. Publ. No. 2009/0018018).

Despite their suggested use in glyphosates, etheramine alkoxylates are generally not miscible with glyphosate or water, and they may not be miscible with other surfactant components. On the other hand, a surfactant blend needs to have good stability in and of itself, and it also needs to impart stability to aqueous glyphosates in which it is formulated.

More recently, we described (U.S. Pat. Appl. Publ. No. 2009/0318294) high-load glyphosate concentrates comprising a fatty amine oxide, a solubilizer (e.g., polyethylene glycol), and a dialkoxylated alkylamine (e.g., a tallowamine surfactant). When the surfactant blend is combined with IPA, potassium, or mixed salt glyphosates, the resulting concentrates are storage stable and have high or no cloud points. The ability to provide such highly concentrated glyphosates, especially with a potassium glyphosate, is valuable. Etheramine alkoxylates are not taught as surfactant components.

Despite the high glyphosate concentration available by choosing a potassium glyphosate (compared with IPA and other amine salts), the K salt is notorious for incompatibility issues with a "wide range" of surfactants (see U.S. Pat. No. 7,316,990 at col. 2 and U.S. Pat. No. 7,135,437 at the paragraph bridging cols. 4 and 5). The '990 patent counsels use of monomethylamine (MMA) or dimethylamine (DMA) salts to enhance compatibility. Other references, such as U.S. Pat. Appl. Publ. No. 2003/0096708, discuss the difficulties in pouring or pumping highly concentrated mixtures of potassium glyphosates (see p. 4, paragraph [0033]).

Formulators of glyphosates frequently struggle with how to maintain high productivity while dealing effectively with heat removal. The exothermic neutralization reaction limits the pace at which glyphosates can be formulated without resort to expensive refrigeration units, and thus limits production rates. It is therefore desirable for formulations to have as high a cloud point as possible. A formulation that has a cloud point of 65° C., for instance, cannot be produced as efficiently as one having a cloud point of 80 or 90° C. because the formulator will have to decelerate the addition of caustic when the temperature approaches 65° C. On the other hand, it can be challenging to identify formulations that are highly concentrated, gel free, stable at elevated temperature, and also have high cloud points.

Interestingly, relatively little appears to be known about how the pH of aqueous glyphosate concentrates might impact the elevated temperature stability of aqueous formulations comprising the concentrates and commonly used surfactants. This is particularly true of highly concentrated potassium glyphosates. U.S. Pat. Appl. Publ. No. 2009/0018018 teaches potassium glyphosate compositions comprising a fatty amine oxide surfactant, an optional water-miscible solvent (N-methyl-2-pyrrolidone in the examples), and other surfactants that could be, e.g., an etheramine alkoxylate or a betaine. Table 1 of the '018 publication reports pH values for the potassium glyphosate plus water and surfactant of about 4.7. U.S. Pat. No. 7,049,270 teaches aqueous potassium glyphosate concentrates having a pH of 4.76 (see Example A, col. 72). U.S. Pat. Appl. Publ. No. 2011/0105328 teaches potassium glyphosate concentrates having a pH range from 5.5 to 11 (see paragraph [0015]). U.S. Pat. Appl. Publ. No. 2011/0009269 reports pH values of 4.5 to 5.0 for an aqueous isopropylamine (IPA) glyphosate concentrate, but alkali metal glyphosates are not discussed. U.S. Pat. Appl. Publ. No. 2010/0113274 teaches the value of amidoamines for enhancing the compatibility of other surfactants (e.g., etheramines, fatty amine oxides) in blends of potassium and monoethanolamine glyphosates. Table 11 (p. 22) lists formulation pH values of about 4.6. U.S. Pat. No. 6,767,863 (Ex. 1) indicates a pH of 4.58 for an IPA glyphosate formulation containing a tallowamine ethoxylate. U.S. Pat. No. 6,475,953 lists pH values of 5 to 7 for IPA or sodium glyphosate formulations that contain soy lecithin and other components (see Table 2a). Thus, although pH is reported for various formulations in these references, there appears to be little or no attempt to control pH to achieve a performance benefit.

U.S. Pat. Appl. Publ. No. 2010/0331182 describes high-strength concentrates of glyphosate and dicamba salts, including potassium salts, for which the pH is adjusted between 6.0 and 8.0 (abstract, Table 1). High strength is achieved provided that a mixture of glyphosate and dicamba salts is used and pH is kept within the target range. U.S. Pat. No. 7,223,718 teaches to adjust pH to 7.0 to 8.5 to achieve a single-phase concentrate comprising a glyphosate di-salt and an enhancement agent.

In sum, the industry would benefit from improved alkali metal glyphosate compositions that are highly concentrated yet have good elevated temperature stability. Of particular interest are compositions based on etheramine alkoxylates, which are less irritating than tallowamine ethoxylates. Also needed are surfactant blends useful in the glyphosate formulations that do not gel or phase separate during storage. Ideally, a variety of surfactants could be used with the etheramine alkoxylates while avoiding the compatibility problems that previously discouraged formulators from opting for alkali metal glyphosates in highly concentrated compositions. Formulators would welcome glyphosate compositions that have, in addition to the other attributes discussed above, high cloud points to allow formulation at relatively high temperatures and without the need for expensive refrigeration.

SUMMARY OF THE INVENTION

In one aspect, the invention relates to an aqueous alkali metal glyphosate composition. The composition comprises: (a) an aqueous concentrate comprising at least 30 wt. % acid equivalents of an alkali metal glyphosate; (b) a surfactant blend comprising an etheramine component; and (c) optionally, a water-miscible solvent. A mixture of the surfactant blend and solvent is gel-free and monophasic. We surprisingly found that by adjusting the pH of the aqueous concentrate to be within the range of 4.0 to 4.5, a highly concentrated aqueous alkali metal glyphosate composition having good elevated temperature stability could be made. In particular, when a 540 g.a.e./L formulation comprising the composition is prepared, it exhibits good stability even at 54° C. The compositions frequently have a high cloud point, which maximizes productivity in the exothermic neutralization step.

In another aspect, the invention relates to a gel-free, monophasic surfactant blend. The blend comprises three components. An etheramine, present at 40 to 50 wt. %, is the first component. It comprises at least 35 wt. % of a first etheramine ethoxylate of the formula:

where R is a linear or branched $C_{10}$-$C_{16}$ alkyl group, AO is a $C_2$-$C_4$ oxyalkylene group, EO is an oxyethylene group, x is 1, and y+z is about 5. The surfactant blend also includes from 5 to 20 wt. % of propylene glycol and from 40 to 50 wt. % of water or a surfactant selected from fatty amine oxides, betaines, and mixtures thereof. The surfactant blends, which are formulated to be gel-free and stable with respect to phase separation, are valuable for making the aqueous alkali metal glyphosate compositions.

DETAILED DESCRIPTION OF THE INVENTION

Aqueous alkali metal glyphosate compositions of the invention comprise an aqueous concentrate of alkali metal glyphosate, a surfactant blend, and an optional solvent. The aqueous concentrate comprises water and at least 30 wt. % acid equivalents, more preferably at least 36 wt. % acid equivalents, and most preferably at least 39 wt. % acid equivalents, of an alkali metal glyphosate. The alkali metal is preferably lithium, sodium or potassium, more preferably sodium or potassium, and most preferably potassium. For potassium glyphosate, 39 wt. % acid equivalents (or 39 wt. % "a.e.") corresponds to about 48 wt. % of the potassium salt because the potassium salt has a higher molecular weight than the acid by a factor of about 1.23. Thus, it takes about 23% by weight more of the potassium salt to deliver the same amount of glyphosate acid as would be provided by the pure acid. (Unfortunately, the acid is relatively insoluble in water!)

Aqueous concentrates used in the glyphosate compositions are typically made by combining glyphosate acid and water. Glyphosate acid is commercially available and can come from any desired source. One common commercial material is supplied at about 90.5% glyphosate acid. A basic alkali metal compound (e.g., potassium hydroxide) is ordinarily added with appropriate cooling to the aqueous glyphosate acid slurry with good mixing to generate the alkali metal glyphosate concentrate.

The surfactant blend comprises an etheramine component. Etheramines are well known in the industry. They have at least one ether functional group and at least one tertiary amine group. Etheramine alkoxylates, especially the ethoxylates, are preferred, and many are commercially available. For instance, Air Products supplies Tomamine™ ethoxylated amines. Preferred etheramine ethoxylates from this series include Tomamine E-14-2, E-14-5, E-17-2, and E-17-5. To illustrate, E-14-2 is bis(2-hydroxyethyl)isodecyloxypropylamine, and E-14-5 is poly(5)oxy-ethylene isodecyloxypropylamine. Suitable etheramine alkoxylates can also be synthesized by reacting a fatty alcohol with acrylonitrile to give an ether nitrile, followed by hydrogenation to the amine and alkoxylation with one or more molar equivalents of ethylene oxide, propylene oxide, or combinations thereof, as is described in U.S. Pat. No. 5,616,811, the teachings of which are incorporated herein by reference. Etheramine ethoxylates having from 2 to 5 oxyethylene units per molecule are especially preferred.

In one aspect, the etheramine component comprises a first etheramine ethoxylate of the formula:

wherein R is a linear or branched $C_{10}$-$C_{16}$ alkyl group, AO is a $C_2$-$C_4$ oxyalkylene group, EO is an oxyethylene group, x is 1, and y+z is about 5.

In another aspect, the etheramine component comprises, in addition to the first etheramine ethoxylate, a second etheramine ethoxylate of the formula:

wherein R is a linear or branched $C_{10}$-$C_{16}$ alkyl group, AO is a $C_2$-$C_4$ oxyalkylene group, EO is an oxyethylene group, x is 1, and y+z is about 2.

Etheramine ethoxylates have become desirable as a less-irritating alternative to ethoxylated tallowamines (see U.S. Pat. No. 5,750,468).

The surfactant blend can include one or more auxiliary surfactants, including cationic, anionic, nonionic, amphoteric, or zwitterionic surfactants, provided that they do not interfere with formulation stability or reduce herbicidal effectiveness. Thus, suitable auxiliary surfactants include aminated alkoxylated alcohols, hydroxylated amides, diamines, mono- and diammonium salts, poly(hydroxyalkyl)amines, alkoxylated poly(hydroxyalkyl)amines, alkyl esters of sucrose or sorbitan, alkyl polyglucosides, quaternary ammonium compounds, amine oxides, alkoxylated amine oxides, betaines, sulfobetaines, and many others. For additional examples of suitable auxiliary surfactants, see U.S. Pat. Nos. 7,135,437 and 7,049,270, the teachings of which related to surfactant classes are incorporated herein by reference.

Among auxiliary surfactants, fatty amine oxides and betaines are preferred. Suitable amine oxides include those having the formula $R^4R^5R^6N \rightarrow O$ wherein $R^4$ is a $C_8$-$C_{24}$, particularly a $C_{12}$-$C_{18}$ straight or branched chain, saturated or unsaturated hydrocarbyl group, such as lauryl, decyl, cetyl, oleyl, stearyl and hexadecyl, or a $R^7CONH(CH_2)_n$ group, wherein $R^7$ is a $C_8$-$C_{24}$, particularly a $C_{12}$-$C_{18}$ straight or branched chain, saturated or unsaturated hydrocarbyl group and n is from 1 to 3; $R^5$ and $R^6$ are independently $C_1$-$C_3$ hydrocarbyl groups such as methyl, ethyl, propyl or substituted $C_1$-$C_3$ hydrocarbyl groups such as hydroxyethyl, hydroxyethoxyethyl and hydroxy polyethoxyethyl. Examples of suitable amine oxides include coconut dimethylamine oxide, capric/capryllic dimethylamine oxide, capric dimethylamine oxide, lauryl dimethylamine oxide, lauryl/myristyl dimethylamidopropylamine oxide, and cocodimethylamidopropylamine oxide. Suitable amine oxides are available commercially as Ammonyx™ LD, Ammonyx CO, Ammonyx DO, Ammonyx 810 DO, Ammonyx MO, and Ammonyx LMDO, all from Stepan Company. Suitable amine oxides can be made by oxidizing the corresponding amine with hydrogen peroxide or other suitable oxidizing agents using well-known methods. Additional suitable amine oxides are disclosed in U.S. Pat. No. 5,710,103, the teachings of which are incorporated herein by reference. As shown in the examples below, amine oxides can provide somewhat wider formulation latitude than betaines when used as the auxiliary surfactant with an etheramine in alkali metal glyphosate compositions.

Suitable betaines have a quaternary nitrogen and carboxylate functionalities, typically separated by one or more alkylene groups. Examples include products available from Stepan Company under the Amphosol™ mark, including Amphosol C series betaines and Amphosol LB, which is laurylamidopropyl betaine. Other suitable betaines are available from Rhodia under the Geranol™, Mirataine®, or Wettem® marks, such as Geranol CF/AS 30, a $C_{12}$-$C_{14}$ alkyldimethylbetaine. For additional examples of suitable betaines, see U.S. Pat. Appl. Publ. No. 2005/0170965, the teachings of which are incorporated herein by reference.

The aqueous alkali metal glyphosate compositions optionally comprise a water-miscible solvent. Suitable solvents have the ability to compatibilize surfactants in the surfactant blend so that a stable, gel-free, monophasic blend is achieved. "Gel-free" means that the composition remains easily stirred and pourable after all surfactant and any solvent components are combined, mixed, and allowed to stand for several hours. "Monophasic" means that there is neither rapid nor gradual separation into two or more liquid phases after all surfactant and any solvent components are combined, mixed, and stored for several days. Preferred solvents are alcohols, glycols, polyalcohols, glycol ethers, glycol ether esters, polyoxyalkylene glycols, and the like, and mixtures thereof. Glycols and polyoxyalkylene glycols such as propylene glycol, dipropylene glycol, triethylene glycol, and lower molecular weight (50 to 1000, preferably from 100 to 600 g/mol) polyethylene glycols are preferred. Propylene glycol is particularly preferred. As shown in Table 1, below, propylene glycol generally provides surfactant blends with etheramine ethoxylates that have little or no tendency to form gels and have a reduced incidence of phase separation when compared with alternative solvents such as polyethylene glycol (Table 2).

As noted earlier, aqueous concentrates are made by combining glyphosate acid, water, and an alkali metal compound, typically an alkali metal hydroxide. After the concentrate is made, the pH of the concentrate is normally determined by preparing a 10% aqueous solution in deionized water and measuring pH using a pH meter that has been calibrated using standard solutions. For purposes of this invention, the pH of the aqueous concentrate (i.e., without added surfactants or solvent) is adjusted to be within the range of 4.0 to 4.5, preferably from 4.1 to 4.5, more preferably from 4.2 to 4.5, and most preferably from 4.3 to 4.4.

We surprisingly found that using an aqueous concentrate a with pH value within the range of 4.0 to 4.5 enables facile production of high-strength alkali metal glyphosate compositions that have excellent elevated temperature stability. In particular, a 540 g.a.e./L potassium glyphosate formulation prepared from such an aqueous concentrate is stable at ambient and elevated temperatures. For convenience, the elevated temperature test is performed at 54° C., which exceeds the maximum storage and mixing temperatures normally used in the field for handling glyphosate formulations. By "stable," we mean that the composition, which includes the aqueous glyphosate concentrate, water, surfactant(s), and any solvent does not phase separate or undergo a substantial change in optical clarity after storage in an oven for 2 weeks at 54° C.

Tables 1-3 below provide a dramatic demonstration of the value of utilizing aqueous glyphosate compositions having a pH in the range of 4.3 to 4.5 versus 4.7 or 4.8. The compositions in Table 1 all use propylene glycol as a solvent. An etheramine ethoxylate sufactant is used alone (Examples A1-A4) or in combination with a fatty amine oxide (Examples A5-A20) or a betaine (Examples A21-A30). Propylene glycol performs exceptionally well in preventing gelation of the surfactant blends (although not all of the surfactant/solvent combinations had long-term stability). Consider, however, the impact of aqueous concentrate pH on the stability of the 540 g.a.e./L potassium glyphosate formulations at 54° C. At pH 4.3, almost every tested composition passes the stability test, whereas the opposite is true at pH 4.8. Similar results are obtained when polyethylene glycol is used as the solvent (Table 2, Examples B1-B30). Because polyethylene glycol is somewhat less forgiving than propylene glycol, especially in preventing surfactant mixtures from gelling, the results are not as dramatic, but the trend is the same. Interestingly, the solvent can even be omitted in some compositions (Table 3, Example C1) without changing the result. When a commercial product, RoundUp® PowerMax (Monsanto) is formulated at the same 540 g.a.e./L level, and pH is adjusted to the same values, composition stability deteriorates at pH 4.8 (see Table 3). The idea of adjusting pH to the 4.0 to 4.5 range to improve formulation stability for high-strength alkali metal glyphosate compositions is not suggested in the voluminous glyphosate literature.

The aqueous alkali metal glyphosate compositions preferably have a cloud point greater than 60° C., more preferably greater than 75° C., even more preferably greater than 85° C., and most preferably greater than 95° C. As noted earlier, when the cloud point is high, formulators can add a neutralizing agent more rapidly without concerns about phase separation and can therefore maintain a high productivity level. Cloud point is conveniently measured by slowly heating a glyphosate composition sample with stirring and noting its temperature while watching for changes in appearance. The temperature at which the solution first becomes cloudy is the cloud point. The inventive alkali metal glyphosate compositions, particularly those formulated at low pH, have exceptionally high cloud points, even showing no phase separation as the mixture approaches boiling (see especially Table 5, pH=4.3 column, Examples A1, A9-A13, A16, A19, and A21-A23).

In another aspect, the invention relates to a gel-free, monophasic surfactant blend. The blend comprises three components. An etheramine, present at 40 to 50 wt. %, more preferably from 42 to 48 wt. %, is the first component. It comprises at least 35 wt. % of a first etheramine ethoxylate of the formula:

where R is a linear or branched $C_{10}$-$C_{16}$ alkyl group, AO is a $C_2$-$C_4$ oxyalkylene group, EO is an oxyethylene group, x is 1, and y+z is about 5. The surfactant blend also includes from 5 to 20 wt. %, preferably from 9 to 17 wt. %, of propylene glycol and from 40 to 50 wt. %, preferably from 42 to 48 wt. % of water or a surfactant selected from fatty amine oxides, betaines, and mixtures thereof. The surfactant blends, which are formulated to be gel-free and stable with respect to phase separation, are valuable for making the aqueous alkali metal glyphosate compositions.

We surprisingly found that propylene glycol provides substantial advantages for formulating a gel-free, monophasic surfactant blend where an etheramine ethoxylate is a surfactant component. Table 1 shows that such surfactant blends have little or no tendency to gel. Additionally, the blends are reasonably stable, at least in the short term, particularly when compared with alternative solvents such as polyethylene glycol (Table 2). We also found that surfactant blends that include propylene glycol and an etheramine ethoxylate having about 5 moles of oxyethylene units per molecule (as in etheramine "C" in Table 1) are usually gel-free, monophasic, and provide stable 540 g.a.e./L potassium glyphosate formulations (see Examples A1, A3, A10, A12, A13, A15, A24, A25, A29, and A30).

In another aspect, the etheramine component of the surfactant blend further comprises a second etheramine ethoxylate of the formula:

wherein R is a linear or branched $C_{10}$-$C_{16}$ alkyl group, AO is a $C_2$-$C_4$ oxyalkylene group, EO is an oxyethylene group, x is 1, and y+z is about 2. See Table 1, Examples A1, A10, A12, A13, A24, A25, A29, and A30, which illustrate this concept.

In another preferred aspect, the surfactant blend or glyphosate composition utilizes an amine oxide as the auxiliary surfactant. These compositions tend to be forgiving in that they require less of the solvent to achieve a high cloud point. To appreciate this, consider the pH=4.3 column of Table 5, and Example A13 (amine oxide) versus Examples A25 or A29 (betaine). At the same level of propylene glycol, A13 has a cloud point>100° C., while A25 is 87° C. and A29 is 74.6° C. This difference of 10 or 20° C. in cloud point may be the difference in having to decelerate addition of neutralizing agent in a commercial production run, which could be costly. As another example, consider the pH=4.5 column in Table 5, and Example A9 (amine oxide) versus Examples A21, A22, and A23 (betaine). Notice that relatively more propylene glycol is needed to get an 88° C. cloud point (A9 versus A23). Again, in Table 5, pH=4.5 column, A12 (amine oxide) required less propylene glycol to get a 74.3° C. cloud point compared with A24 (betaine) in arriving at a 64.9° C. cloud point.

In yet another aspect, the invention relates to a method of making the surfactant blends. The method comprises combining, in any desired order, (a) the etheramine component; (b) propylene glycol; and (c) water or a fatty amine or betaine surfactant. We found that either order of addition consistently affords good results in terms of avoiding gel formation and phase separation when propylene glycol is used as the solvent (see Table 7). With PEG, the same formulations frequently gelled or phase separated (see Table 2).

The following examples merely illustrate the invention. Those skilled in the art will recognize many variations that are within the spirit of the invention and scope of the claims.

Preparation of Aqueous Potassium Glyphosate Concentrates

EXAMPLE 1

Preparation of Potassium Glyphosate, pH=4.3

Glyphosate acid (90.5%, 485.95 g) is added to an ice-cooled beaker, and deionized water (342.52 g) is added with mixing to create a slurry. Potassium hydroxide pellets (86.6+%, 71.53 g) are slowly added while mixing to generate potassium glyphosate concentrate (44.0% acid equivalents, 1000 g). The final pH of this concentrate, measured as a 10% solution in deionized water (using a pH meter calibrated with commercial standards), is 4.3.

EXAMPLE 2

Preparation of Potassium Glyphosate, pH=4.5

The procedure of Example 1 is followed using 486.19 g of glyphosate acid, 323.23 g of deionized water, and 190.58 g of KOH pellets. The resulting potassium glyphosate concentrate (1000 g) has 44.0% acid equivalents. The final pH of the concentrate, measured as a 10% solution in deionized water, is 4.5.

EXAMPLE 3

Preparation of Potassium Glyphosate, pH=4.8

The procedure of Example 1 is followed using 519.30 g of glyphosate acid, 324.20 g of deionized water, and 224.60 g KOH pellets. The resulting potassium glyphosate concentrate (1068.10 g) has 44.0% acid equivalents. The final pH of the concentrate, measured as a 10% solution in deionized water, is 4.8.

A commercial sample of potassium glyphosate concentrate is used as received. Measured as described above, the concentrate has pH=4.7.

Preparation of Surfactant Blends

Surfactant blends are prepared by combining the desired etheramine ethoxylate (see Table 1) with a water-miscible solvent (propylene glycol or PEG 200). This mixture is then combined with the auxiliary surfactant (amine oxide or betaine) or water. The blends are evaluated for gel formation and phase separation. Gel formation is deemed to have occurred if the mixture cannot be stirred or becomes unpourable within 1 day. Some blends rapidly separate into two phases (reported as "fast"), while the separation is more gradual and subtle in others ("slow"). If no phase separation is observed over several days, the blend is considered stable. Samples that gel or produce two phases are not further evaluated.

Stability of 540 g.a.e./L Formulations at 54° C.

A high-load potassium glyphosate concentrate is prepared by adding a surfactant blend to an aqueous concentrate prepared as described earlier and mixing well. A 50-g sample of the concentrate is placed in an oven at 54° C. for 2 weeks. If the concentrate does not separate or undergo a substantial change in optical clarity, it is deemed to have warm temperature stability. Stability results as a function of aqueous concentrate pH are reported in Tables 1-3.

Cloud Point Determination

Cloud point readings are taken by placing about 25 g of high-load potassium glyphosate concentrate (including the surfactant blend) in a container with a stir bar. The lid of the container is equipped with an adapter and thermometer. The solution is heated with stirring, and the temperature at which the solution first becomes cloudy is noted as the cloud point. Tables 4-6 provide cloud point data as a function of pH for formulations tested.

The preceding examples are meant only as illustrations; the following claims define the invention.

TABLE 1

Glyphosate Compositions using Propylene Glycol: Effect of pH on 540 g/L K Formulation Stability

| | Etheramine ethoxylate[1], g | | | | Solvent | Aux. Surfactant[2], g | | | | Surfactant + Solvent[3] | | Stable 540 g/L K salt at 54° C.? | | | |
|---|---|---|---|---|---|---|---|---|---|---|---|---|---|---|---|
| | A | B | C | D | PG, g | X | Y | Z | $H_2O$, g | Gel? | Separates? | pH 4.3 | pH 4.5 | pH 4.7 | pH 4.8 |
| A1 | | 2 | 3 | | 1.3 | | | | 5 | N | N | Y | Y | — | N |
| A2* | | | 5 | | 1.3 | | | | 5 | N | Fast | — | — | — | — |
| A3 | | 5 | | | 1.3 | | | | 5 | N | N | Y | N | — | N |
| A4* | | 5 | | | 2 | | | | 5 | N | Fast | — | — | — | — |
| A5 | 4 | | | | 2 | 4 | | | | N | N | Y | N | — | N |
| A6 | 4.5 | | | | 1 | 4.5 | | | | N | N | Y | N | — | N |
| A7* | 4.75 | | | | 0.5 | 4.75 | | | | N | Slow | — | — | — | — |
| A8* | | 5 | | | 2 | 5 | | | | Y | N | — | — | — | — |
| A9 | | | 5 | | 2 | 5 | | | | N | N | Y | Y | — | N |
| A10 | | | 2.5 | 2.5 | 1 | 5 | | | | N | N | Y | Y | — | N |
| A11 | 2.5 | | | 2.5 | 1.5 | 5 | | | | N | N | Y | Y | — | N |
| A12 | | 2 | 3 | | 1.1 | 5 | | | | N | N | Y | Y | — | N |
| A13 | | 2 | 3 | | 1.3 | 5 | | | | N | N | Y | Y | — | N |
| A14* | | | 5 | | 1.3 | 5 | | | | N | Slow | — | — | — | — |
| A15 | 5 | | | | 1.3 | 5 | | | | N | N | Y | Y | — | N |
| A16 | | | 5 | | 1.5 | 5 | | | | N | N | Y | Y | Y | N |
| A17* | | | 4 | | 1.4 | 6 | | | | N | Slow | — | — | — | — |
| A18* | | | 4 | | 1.5 | 6 | | | | N | Slow | — | — | — | — |
| A19 | | | 3 | | 1.5 | 7 | | | | N | N | Y | Y | Y | N |
| A20* | | | 3 | | 1.25 | 7 | | | | N | Slow | — | — | — | — |
| A21 | | | 5 | | 2 | | 5 | | | N | N | Y | N | — | N |
| A22 | | | 4 | | 2 | | 4 | | | N | N | Y | Y | — | N |
| A23 | | | 4 | | 3 | | 4 | | | N | N | Y | Y | — | N |
| A24 | | 2 | 3 | | 2 | | 5 | | | N | N | Y | Y | — | N |
| A25 | | 2 | 3 | | 1.3 | | 5 | | | N | N | Y | N | — | N |
| A26* | | 5 | | | 2 | | 5 | | | N | N | N | N | — | N |
| A27 | | | 5 | | 2 | | | 5 | | N | N | Y | N | — | N |
| A28 | | | 4 | | 2 | | | 4 | | N | N | Y | N | — | N |
| A29 | | 2 | 3 | | 1.3 | | | 5 | | N | N | Y | N | — | N |
| A30 | | | 2.5 | 2.5 | 1.3 | | | 5 | | N | N | Y | N | — | N |

[1]Etheramine ethoxylates: A = E-17-5; B = E-17-2; C = E-14-5; D = E-14-2, all products of Tomah
[2]Surfactants: X = Ammonyx LO, product of Stepan; Y = Amphosol LB, product of Stepan; Z = Geranol CF/AS 30, product of Rhodia
[3]Surfactant + solvent were gel-free with no separation to be considered suitable for evaluation of a 540 g/L potassium glyphosate formulation.
*Comparative examples

TABLE 2

Glyphosate Compositions using Polyethylene Glycol: Effect of pH on 540 g/L K Formulation Stability

| | Etheramine ethoxylate[1], g | | | | Solvent | Aux. Surfactant[2], g | | | | Surfactant + Solvent[3] | | Stable 540 g/L K salt at 54° C.? | | | |
|---|---|---|---|---|---|---|---|---|---|---|---|---|---|---|---|
| | A | B | C | D | PEG, g | X | Y | Z | $H_2O$, g | Gel? | Separates? | pH 4.3 | pH 4.5 | pH 4.7 | pH 4.8 |
| B1* | | 2 | 3 | | 1.3 | | | | 5 | N | Fast | — | — | — | — |
| B2* | | | 5 | | 1.3 | | | | 5 | N | Fast | — | — | — | — |
| B3 | | 5 | | | 1.3 | | | | 5 | N | N | Y | N | — | N |
| B4* | | 5 | | | 2 | | | | 5 | N | Fast | — | — | — | — |
| B5 | 4 | | | | 2 | 4 | | | | N | N | Y | N | N | N |
| B6 | 4.5 | | | | 1 | 4.5 | | | | N | N | Y | N | N | N |
| B7* | 4.75 | | | | 0.5 | 4.75 | | | | N | Slow | — | — | — | — |
| B8* | | 5 | | | 2 | 5 | | | | Y | N | — | — | — | — |
| B9 | | | 5 | | 2 | 5 | | | | N | N | Y | Y | Y | N |
| B10* | | | 2.5 | 2.5 | 1 | 5 | | | | N | Slow | — | — | — | — |
| B11* | 2.5 | | | 2.5 | 1.5 | 5 | | | | N | Slow | — | — | — | — |
| B12* | | 2 | 3 | | 1.1 | 5 | | | | N | Slow | — | — | — | — |
| B13* | | 2 | 3 | | 1.3 | 5 | | | | N | Slow | — | — | — | — |
| B14* | | | 5 | | 1.3 | 5 | | | | Y | N | — | — | — | — |

TABLE 2-continued

Glyphosate Compositions using Polyethylene Glycol: Effect of pH on 540 g/L K Formulation Stability

| | Etheramine ethoxylate[1], g | | | | Solvent | Aux. Surfactant[2], g | | | | Surfactant + Solvent[3] | | Stable 540 g/L K salt at 54° C.? | | | |
|---|---|---|---|---|---|---|---|---|---|---|---|---|---|---|---|
| | A | B | C | D | PEG, g | X | Y | Z | H$_2$O, g | Gel? | Separates? | pH 4.3 | pH 4.5 | pH 4.7 | pH 4.8 |
| B15 | | 5 | | | 1.3 | 5 | | | | N | N | Y | Y | N | N |
| B16* | | | 5 | | 1.5 | 5 | | | | Y | N | — | — | — | — |
| B17* | | | | 4 | 1.4 | 6 | | | | Y | N | — | — | — | — |
| B18* | | | | 4 | 1.5 | 6 | | | | Y | N | — | — | — | — |
| B19* | | | | 3 | 1.5 | 7 | | | | Y | N | — | — | — | — |
| B20* | | | | 3 | 1.25 | 7 | | | | Y | N | — | — | — | — |
| B21* | | | 5 | | 2 | | 5 | | | Y | N | — | — | — | — |
| B22* | | | | 4 | 2 | | 4 | | | Y | N | — | — | — | — |
| B23 | | | | 4 | 3 | | 4 | | | N | N | Y | Y | N | N |
| B24* | | 2 | 3 | | 2 | | 5 | | | N | Slow | — | — | — | — |
| B25* | | 2 | 3 | | 1.3 | | 5 | | | Y | N | — | — | — | — |
| B26* | | 5 | | | 2 | | 5 | | | N | N | N | N | N | N |
| B27* | | | 5 | | 2 | | | 5 | | Y | N | — | — | — | — |
| B28* | | | | 4 | 2 | | | 4 | | N | Slow | — | — | — | — |
| B29* | | 2 | 3 | | 1.3 | | | 5 | | N | Slow | — | — | — | — |
| B30* | | 2.5 | 2.5 | | 1.3 | | | 5 | | N | Slow | — | — | — | — |

[1]Etheramine ethoxylates: A = E-17-5; B = E-17-2; C = E-14-5; D = E-14-2, all products of Tomah
[2]Surfactants: X = Ammonyx LO, product of Stepan; Y = Amphosol LB, product of Stepan; Z = Geranol CF/AS 30, product of Rhodia
[3]Surfactant + solvent were gel-free with no separation to be considered suitable for evaluation of a 540 g/L potassium glyphosate formulation.
*Comparative examples

TABLE 3

Glyphosate Compositions using No Solvent: Effect of pH on 540 g/L K Formulation Stability

| | Etheramine ethoxylate[1], g | | | | Aux. Surfactant[2], g | | | | Surfactant + Solvent[3] | | Stable 540 g/L K salt at 54° C.? | | | |
|---|---|---|---|---|---|---|---|---|---|---|---|---|---|---|
| | A | B | C | D | X | Y | Z | H$_2$O, g | Gel? | Separates? | pH 4.3 | pH 4.5 | pH 4.7 | pH 4.8 |
| C1 | | | 5 | | 5 | | | | N | N | Y | Y | N | N |
| C2* | 5 | | | | 5 | | | | Y | N | — | — | — | — |
| Roundup PowerMax | | | | | | | | | | | Y | Y | Y | N |

[1]Etheramine ethoxylates: A = E-17-5; B = E-17-2; C = E-14-5; D = E-14-2, all products of Tomah
[2]Surfactants: X = Ammonyx LO, product of Stepan; Y = Amphosol LB, product of Stepan; Z = Geranol CF/AS 30, product of Rhodia
[3]Surfactant + solvent were gel-free with no separation to be considered suitable for evaluation of a 540 g/L potassium glyphosate formulation.
*Comparative example

TABLE 4

Glyphosate Compositions using No Solvent: Cloud Points for 540 g/L K Formulations

| | Etheramine ethoxylate[1], g | | | | Aux. Surfactant[2], g | | | | Surfactant + Solvent[3] | | Cloud Point (° C.) | | | |
|---|---|---|---|---|---|---|---|---|---|---|---|---|---|---|
| | A | B | C | D | X | Y | Z | H$_2$O, g | Gel? | Separates? | pH 4.3 | pH 4.5 | pH 4.7 | pH 4.8 |
| C1 | | | 5 | | 5 | | | | N | N | 87.2 | 59.5 | — | — |
| C2* | 5 | | | | 5 | | | | Y | N | — | — | — | — |
| RoundUp PowerMax | | | | | | | | | | | — | — | 74.5 | — |

[1]Etheramine ethoxylates: A = E-17-5; B = E-17-2; C = E-14-5; D = E-14-2, all products of Tomah
[2]Surfactants: X = Ammonyx LO, product of Stepan; Y = Amphosol LB, product of Stepan; Z = Geranol CF/AS 30, product of Rhodia
[3]Surfactant + solvent were gel-free with no separation to be considered suitable for evaluation of a 540 g/L potassium glyphosate formulation.
*Comparative example

TABLE 5

Glyphosate Compositions using Propylene Glycol: Cloud Points for 540 g/L K Formulations

| | Etheramine ethoxylate[1], g | | | | Solvent | Aux. Surfactant[2], g | | | | Surfactant + Solvent[3] | | Cloud Point (° C.) | | | |
|---|---|---|---|---|---|---|---|---|---|---|---|---|---|---|---|
| | A | B | C | D | PG, g | X | Y | Z | H₂O, g | Gel? | Separates? | pH 4.3 | pH 4.5 | pH 4.7 | pH 4.8 |
| A1 | | | 2 | 3 | 1.3 | | | | 5 | N | N | >100 | 83.9 | — | — |
| A2* | | | | 5 | 1.3 | | | | 5 | N | Fast | — | — | — | — |
| A3 | | | 5 | | 1.3 | | | | 5 | N | N | 88.2 | — | — | — |
| A4* | | 5 | | | 2 | | | | 5 | N | Fast | — | — | — | — |
| A5 | 4 | | | | 2 | 4 | | | | N | N | 85.1 | — | — | — |
| A6 | 4.5 | | | | 1 | 4.5 | | | | N | N | 79.0 | — | — | — |
| A7* | 4.75 | | | | 0.5 | 4.75 | | | | N | Slow | — | — | — | — |
| A8* | | 5 | | | 2 | 5 | | | | Y | N | — | — | — | — |
| A9 | | | | 5 | 2 | 5 | | | | N | N | >100 | 88.9 | — | — |
| A10 | | | 2.5 | 2.5 | 1 | 5 | | | | N | N | >100 | 70.0 | — | — |
| A11 | 2.5 | | | 2.5 | 1.5 | 5 | | | | N | N | 100 | 72.3 | — | — |
| A12 | | | 2 | 3 | 1.1 | 5 | | | | N | N | >100 | 74.3 | — | — |
| A13 | | | 2 | 3 | 1.3 | 5 | | | | N | N | >100 | separates | — | — |
| A14* | | | | 5 | 1.3 | 5 | | | | N | Slow | — | — | — | — |
| A15 | | 5 | | | 1.3 | 5 | | | | N | N | 94.2 | 64.9 | — | — |
| A16 | | | 5 | | 1.5 | 5 | | | | N | N | >100 | 81.6 | 65.0 | — |
| A17* | | | | 4 | 1.4 | 6 | | | | N | Slow | — | — | — | — |
| A18* | | | 4 | | 1.5 | 6 | | | | N | Slow | — | — | — | — |
| A19 | | | | 3 | 1.5 | 7 | | | | N | N | >100 | 93.8 | 76.4 | — |
| A20* | | | 3 | | 1.25 | 7 | | | | N | Slow | — | — | — | — |
| A21 | | | | 5 | 2 | | 5 | | | N | N | >100 | — | — | — |
| A22 | | | | 4 | 2 | | 4 | | | N | N | >100 | 69.8 | — | — |
| A23 | | | | 4 | 3 | | 4 | | | N | N | >100 | 88.4 | — | — |
| A24 | | | 2 | 3 | 2 | | 5 | | | N | N | 94.8 | 64.9 | — | — |
| A25 | | | 2 | 3 | 1.3 | | 5 | | | N | N | 87.0 | — | — | — |
| A26* | | 5 | | | 2 | | 5 | | | N | N | — | — | — | — |
| A27 | | | | 5 | 2 | | | 5 | | N | N | 97.1 | — | — | — |
| A28 | | | 4 | | 2 | | | 4 | | N | N | 94.2 | — | — | — |
| A29 | | | 2 | 3 | 1.3 | | | 5 | | N | N | 74.6 | — | — | — |
| A30 | | | 2.5 | 2.5 | 1.3 | | | 5 | | N | N | 74.3 | — | — | — |

[1]Etheramine ethoxylates: A = E-17-5; B = E-17-2; C = E-14-5; D = E-14-2, all products of Tomah
[2]Surfactants: X = Ammonyx LO, product of Stepan; Y = Amphosol LB, product of Stepan; Z = Geranol CF/AS 30, product of Rhodia
[3]Surfactant + solvent were gel-free with no separation to be considered suitable for evaluation of a 540 g/L potassium glyphosate formulation.
*Comparative examples

TABLE 6

Glyphosate Compositions using Polyethylene Glycol: Cloud Points for 540 g/L K Formulations

| | Etheramine ethoxylate[1], g | | | | Solvent | Aux. Surfactant[2], g | | | | Surfactant + Solvent[3] | | Cloud Point (° C.) | | | |
|---|---|---|---|---|---|---|---|---|---|---|---|---|---|---|---|
| | A | B | C | D | PEG, g | X | Y | Z | H₂O, g | Gel? | Separates? | pH 4.3 | pH 4.5 | pH 4.7 | pH 4.8 |
| B1* | | | 2 | 3 | 1.3 | | | | 5 | N | Fast | — | — | — | — |
| B2* | | | | 5 | 1.3 | | | | 5 | N | Fast | — | — | — | — |
| B3 | | | 5 | | 1.3 | | | | 5 | N | N | 70.5 | — | — | — |
| B4* | | 5 | | | 2 | | | | 5 | N | Fast | — | — | — | — |
| B5 | 4 | | | | 2 | 4 | | | | N | N | 73.9 | — | — | — |
| B6 | 4.5 | | | | 1 | 4.5 | | | | N | N | 74.5 | — | — | — |
| B7* | 4.75 | | | | 0.5 | 4.75 | | | | N | Slow | — | — | — | — |
| B8* | | 5 | | | 2 | 5 | | | | Y | N | — | — | — | — |
| B9 | | | | 5 | 2 | 5 | | | | N | N | >100 | 87.8 | 65.0 | — |
| B10* | | | 2.5 | 2.5 | 1 | 5 | | | | N | Slow | — | — | — | — |
| B11* | 2.5 | | | 2.5 | 1.5 | 5 | | | | N | Slow | — | — | — | — |
| B12* | | | 2 | 3 | 1.1 | 5 | | | | N | Slow | — | — | — | — |
| B13* | | | 2 | 3 | 1.3 | 5 | | | | N | Slow | — | — | — | — |
| B14* | | | | 5 | 1.3 | 5 | | | | Y | N | — | — | — | — |
| B15 | | 5 | | | 1.3 | 5 | | | | N | N | 84.9 | 54.6 | — | — |
| B16* | | | 5 | | 1.5 | 5 | | | | Y | N | — | — | — | — |
| B17* | | | | 4 | 1.4 | 6 | | | | Y | N | — | — | — | — |
| B18* | | | 4 | | 1.5 | 6 | | | | Y | N | — | — | — | — |
| B19* | | | | 3 | 1.5 | 7 | | | | Y | N | — | — | — | — |
| B20* | | | 3 | | 1.25 | 7 | | | | Y | N | — | — | — | — |
| B21* | | | | 5 | 2 | | 5 | | | Y | N | — | — | — | — |
| B22* | | | | 4 | 2 | | 4 | | | Y | N | — | — | — | — |
| B23 | | | | 4 | 3 | | 4 | | | N | N | 99.8 | 73.5 | — | — |
| B24* | | | 2 | 3 | 2 | | 5 | | | N | Slow | — | — | — | — |
| B25* | | | 2 | 3 | 1.3 | | 5 | | | Y | N | — | — | — | — |

TABLE 6-continued

Glyphosate Compositions using Polyethylene Glycol: Cloud Points for 540 g/L K Formulations

| | Etheramine ethoxylate[1], g | | | | Solvent | Aux. Surfactant[2], g | | | | Surfactant + Solvent[3] | | Cloud Point (° C.) | | | |
|---|---|---|---|---|---|---|---|---|---|---|---|---|---|---|---|
| | A | B | C | D | PEG, g | X | Y | Z | $H_2O$, g | Gel? | Separates? | pH 4.3 | pH 4.5 | pH 4.7 | pH 4.8 |
| B26* | | 5 | | 2 | 5 | | | | | N | N | — | — | — | — |
| B27* | | | 5 | 2 | | | 5 | | | Y | N | — | — | — | — |
| B28* | | | | 4 | 2 | | | 4 | | N | Slow | — | — | — | — |
| B29* | | 2 | 3 | 1.3 | | | | 5 | | N | Slow | — | — | — | — |
| B30* | | 2.5 | 2.5 | 1.3 | | | | 5 | | N | Slow | — | — | — | — |

[1]Etheramine ethoxylates: A = E-17-5; B = E-17-2; C = E-14-5; D = E-14-2, all products of Tomah
[2]Surfactants: X = Ammonyx LO, product of Stepan; Y = Amphosol LB, product of Stepan; Z = Geranol CF/AS 30, product of Rhodia
[3]Surfactant + solvent were gel-free with no separation to be considered suitable for evaluation of a 540 g/L potassium glyphosate formulation.
*Comparative examples

TABLE 7

Effect of Order of Addition for Making Surfactant Blends using Propylene Glycol

| Formula | Step 1 | Step 2 | Step 3 | Result | Step 4 | Step 5 | Result |
|---|---|---|---|---|---|---|---|
| A1 | Combine the etheramine ethoxylates: 2 g of E-14-5 and 3 g of E-14-2 | Add 5 g $H_2O$ | Mix | Gel | Add 1.3 g PG | Mix | Fluid |
| | | Add 1.3 g PG | Mix | Fluid | Add 5 g $H_2O$ | Mix | Fluid |
| A13 | | Add 5 g Ammonyx LO | Mix | Gel | Add 1.3 g PG | Mix | Fluid |
| | | Add 1.3 g PG | Mix | Fluid | Add 5 g Ammonyx LO | Mix | Fluid |
| A25 | | Add 5 g Amphosol LB | Mix | Gel | Add 1.3 g PG | Mix | Fluid |
| | | Add 1.3 g PG | Mix | Fluid | Add 5 g Amphosol LB | Mix | Fluid |
| A29 | | Add 5 g Geranol CF/AS 30 | Mix | Gel | Add 1.3 g PG | Mix | Fluid |
| | | Add 1.3 g PG | Mix | Fluid | Add 5 g Geranol CF/AS 30 | Mix | Fluid |
| A9 | Add 5 g of E-14-2 | Add 5 g Ammonyx LO | Mix | Gel | Add 2 g PG | Mix | Fluid |
| | | Add 2 g PG | Mix | Fluid | Add 5 g Ammonyx LO | Mix | Fluid |
| A21 | | Add 5 g Amphosol LB | Mix | Gel | Add 2 g PG | Mix | Fluid |
| | | Add 2 g PG | Mix | Fluid | Add 5 g Amphosol LB | Mix | Fluid |
| A27 | | Add 5 g Geronol CF/AS 30 | Mix | Gel | Add 2 g PG | Mix | Fluid |
| | | Add 2 g PG | Mix | Fluid | Add 5 g Geronol CF/AS 30 | Mix | Fluid |

In each example, mixing involves shaking the components in a vial and stirring magnetically for 5 min. All of the tested samples provide a gel-free, monophasic fluid after all components are combined and mixed.
E-14-2 and E-14-5 etheramine ethoxylates are products of Tomah. Ammonyx LO and Amphosol LB are products of Stepan Company. Geranol CF/AS 30 is a product of Rhodia.

I claim:

1. An aqueous alkali metal glyphosate composition comprising:
    (a) an aqueous concentrate comprising at least 30 wt. % acid equivalents of an alkali metal glyphosate;
    (b) a surfactant blend comprising an etheramine component; and
    (c) a water-miscible solvent selected from water, propylene glycol and polyethylene glycols and mixtures thereof;
wherein a mixture of the surfactant blend and solvent is gel-free and monophasic, the pH of the aqueous concentrate is adjusted to be within the range of 4.0 to 4.5, and a 540 g.a.e. glyphosate/L formulation comprising the composition is stable at 54° C.

2. The composition of claim 1 comprising at least 36 wt. % acid equivalents of the alkali metal glyphosate.

3. The composition of claim 1 wherein the etheramine component comprising an etheramine ethoxylate comprises a first etheramine ethoxylate of the formula:

R-(AO)$_x$—N[(EO)$_y$—H](EO)$_z$—H wherein R is a linear or branched $C_{10}$-$C_{16}$ alkyl group, AO is a $C_2$-$C_4$ oxyalkylene group, EO is an oxyethylene group, x is 1, and y+z is about 5.

4. The composition of claim 1 wherein the solvent is selected from the group consisting of propylene glycol, polyethylene glycols, and mixtures thereof.

5. The composition of claim 1 wherein the surfactant blend further comprises a fatty amine oxide or betaine.

6. The composition of claim 1 wherein the pH of the aqueous concentrate is adjusted to be within the range of 4.3 to 4.5.

7. The composition of claim 1 having a cloud point greater than 75° C.

8. The composition of claim 1 wherein the alkali metal is potassium.

9. A gel-free, monophasic surfactant blend comprising:
    (a) from 40 to 50 wt. % of an etheramine component, the component comprising at least 35 wt. %, based on the amount of etheramine component, of a first etheramine ethoxylate of the formula:

R-(AO)$_x$—N[(EO)$_y$—H](EO)$_z$—H wherein R is a linear or branched $C_{10}$-$C_{16}$ alkyl group, AO is a $C_2$-$C_4$ oxyalkylene group, EO is an oxyethylene group, x is 1, and y+z is about 5;
    (b) from 5 to 20 wt. % of propylene glycol; and
    (c) from 40 to 50 wt. % of water or a surfactant selected from the group consisting of fatty amine oxides, betaines, and mixtures thereof.

10. The surfactant blend of claim 9 comprising from 9 to 17 wt. % propylene glycol.

11. The surfactant blend of clam 9 wherein the fatty amine oxide comprises a linear or branched $C_8$-$C_{24}$ group.

12. The surfactant blend of claim 9 wherein the fatty amine oxide is lauryl dimethylamine oxide.

13. A method of making the surfactant blend of claim 9, comprising combining: (a) the etheramine component; (b) propylene glycol; and (c) water or the fatty oxide or betaine surfactant in any order.

14. An alkali metal glyphosate composition comprising a gel-free, monophasic surfactant blend, the surfactant blend comprising:
(a) from 40 to 50 wt. % of an etheramine component, the component comprising at least 35 wt. %, based on the amount of etheramine component, of a first etheramine ethoxylate of the formula:

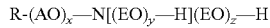

R-(AO)$_x$—N[(EO)$_y$—H](EO)$_z$—H wherein R is a linear or branched $C_{10}$-$C_{16}$ alkyl group, AO is a $C_2$-$C_4$ oxyalkylene group,
EO is an oxyethylene group, x is 1, and y+z is about 5;
(b) from 5 to 20 wt. % of propylene glycol; and
(c) from 40 to 50 wt. % of water or a surfactant selected from the group consisting of fatty amine oxides, betaines, and mixtures thereof.

15. The composition of claim 4 wherein the solvent is propylene glycol.

16. The surfactant blend of claim 9 wherein the etheramine component further comprises a second etheramine ethoxylate of the formula:

R-(AO)$_x$—N[(EO)$_y$—H](EO)$_y$—H wherein R is a linear or branched $C_{12}$-$C_{16}$ alkyl group, AO is a $C_2$-$C_4$ oxyalkylene group, EO is an oxyethylene group, x is 1, and y+z is about 2.

17. An aqueous alkali metal glyphosate composition comprising:
(a) an aqueous concentrate comprising at least 30 wt. % acid equivalents of alkali metal glyphosate;
(b) a surfactant blend comprising an etheramine component comprising an etheramine ethoxylate; and
(c) propylene glycol;
wherein a mixture of the surfactant blend and propylene glycol is gel-free and monophasic, the pH of the aqueous concentrate is adjusted to be within the range of 4.3 to 4.5, and a 540 g.a.e. glyphosate/L formulation comprising the composition is stable at 54° C.

18. The composition of claim 17 wherein the alkali metal is potassium.

19. The composition of claim 17 comprising at least 36 wt. % acid equivalents of the alkali metal glyphosate.

20. The composition of claim 17 wherein the etheramine component comprises a first etheramine ethoxylate of the formula:

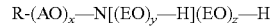

R-(AO)$_x$—N[(EO)$_y$—H](EO)$_z$—H wherein R is a linear or branched $C_{10}$-$C_{16}$ alkyl group, AO is a $C_2$-$C_4$ oxyalkylene group, EO is an oxyethylene group, x is 1, and y+z is about 5.

21. The composition of claim 17 wherein the surfactant blend further comprises a fatty amine oxide or betaine.

* * * * *

UNITED STATES PATENT AND TRADEMARK OFFICE
CERTIFICATE OF CORRECTION

PATENT NO. : 8,455,396 B2
APPLICATION NO. : 13/179775
DATED : June 4, 2013
INVENTOR(S) : Andrew Malec It is certified that error appears in the above-identified patent and that said Letters Patent is hereby corrected as shown below:

In the Claims

Col. 15, claim 1, line 6, after "component" insert --comprising an etheramine ethoxylate--.

Col. 15, claim 3, line 2, after "component" delete "comprising an etheramine ethoxylate".

Signed and Sealed this
Seventeenth Day of September, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,455,396 B2
APPLICATION NO. : 13/179775
DATED : June 4, 2013
INVENTOR(S) : Andrew Malec Page 1 of 1

It is certified that error appears in the above-identified patent and that said Letters Patent is hereby corrected as shown below:

In the Claims

Col. 15 (claim 1, lines 45-46) after "component" insert --comprising an etheramine ethoxylate--.

Col. 15 (claim 3, line 57) after "component" delete "comprising an etheramine ethoxylate".

This certificate supersedes the Certificate of Correction issued September 17, 2013.

Signed and Sealed this
Fifteenth Day of October, 2013

Teresa Stanek Rea
*Deputy Director of the United States Patent and Trademark Office*